(12) United States Patent
Drew et al.

(10) Patent No.: US 6,585,855 B2
(45) Date of Patent: Jul. 1, 2003

(54) PAPER PRODUCT HAVING IMPROVED FUZZ-ON-EDGE PROPERTY

(75) Inventors: Robert A. Drew, Sherwood; Patricia Riedl, Menasha; Peter J. Allen, Neenah, all of WI (US); Brian Klaubert, Tulsa, OK (US); Paul Arnold, Liverdun (FR); Susan E. Smith, Appleton, WI (US); Michael A. Hermans, Neenah, WI (US); Phil S. Lin, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/854,145

(22) Filed: May 11, 2001

(65) Prior Publication Data

US 2002/0088592 A1 Jul. 11, 2002

Related U.S. Application Data

(60) Provisional application No. 60/204,083, filed on May 12, 2000.

(51) Int. Cl.[7] ............................ D21H 27/00; A61F 13/00
(52) U.S. Cl. ........................ 162/109; 162/111; 428/153; 428/154
(58) Field of Search ........................ 162/109, 111, 162/207; 428/153, 154

(56) References Cited

U.S. PATENT DOCUMENTS

| | | |
|---|---|---|
| 3,207,657 A | 9/1965 | Wagner et al. |
| 3,879,257 A | 4/1975 | Gentile et al. |
| 3,903,342 A | 9/1975 | Roberts, Jr. |
| 3,994,771 A | 11/1976 | Morgan, Jr. et al. |
| 4,166,001 A | 8/1979 | Dunning et al. |
| 4,300,981 A | 11/1981 | Carstens |
| 4,309,246 A | 1/1982 | Hulit et al. |
| 4,344,818 A | 8/1982 | Nuttall et al. |
| 4,529,480 A | 7/1985 | Trokhan |
| 4,637,859 A | 1/1987 | Trokhan |
| 5,129,988 A | 7/1992 | Farrington, Jr. |
| 5,230,776 A | 7/1993 | Andersson et al. |
| 5,494,554 A | 2/1996 | Edwards et al. |
| 5,529,665 A | 6/1996 | Kaun |

(List continued on next page.)

FOREIGN PATENT DOCUMENTS

| | | |
|---|---|---|
| CA | 2241820 | 2/1999 |
| EP | 0613979 A1 | 9/1994 |
| EP | 0539703 B1 | 3/1997 |
| EP | 0618329 B1 | 8/1999 |
| EP | 0675225 B1 | 2/2000 |
| WO | WO 9513424 | 5/1995 |
| WO | WO 0008253 A1 | 2/2000 |

OTHER PUBLICATIONS

International Search Report Mailed Dec. 21, 2001 International Filing Date Nov. 5, 2001.

*Primary Examiner*—Dean T. Nguyen
(74) *Attorney, Agent, or Firm*—Dority & Manning, P.A.

(57) ABSTRACT

A process for increasing the tactile properties of a base web without adversely effecting the strength of the web is disclosed. In one embodiment, the process includes the steps of placing a base web between a first moving conveyor and a second moving conveyor. The conveyors are then wrapped around a shear-inducing roll which creates shear forces that act upon the base web. The shear forces disrupt the web, increasing the softness and decreasing the stiffness of the web. The shear-inducing roll typically has a relatively small diameter. In some applications, more than one shear-inducing roll may be incorporated into the system. Base webs made according to the present invention have been found to have improved void-volume and fuzz-on-edge properties.

31 Claims, 11 Drawing Sheets

U.S. PATENT DOCUMENTS

| | | |
|---|---|---|
| 5,562,805 A | 10/1996 | Kamps et al. |
| 5,656,132 A | 8/1997 | Farrington, Jr. et al. |
| 5,672,248 A | 9/1997 | Wendt et al. |
| 5,695,607 A | 12/1997 | Oriaran et al. |
| 5,759,346 A | 6/1998 | Vinson |
| 5,851,629 A | 12/1998 | Oriaran et al. |
| 5,882,479 A | 3/1999 | Oriaran et al. |
| 5,932,068 A | 8/1999 | Farrington, Jr. et al. |
| 5,958,185 A | 9/1999 | Vinson et al. |
| 6,017,418 A | 1/2000 | Oriaran et al. |
| 6,033,523 A | 3/2000 | Dwiggins et al. |
| 6,033,761 A | 3/2000 | Dwiggins et al. |
| 6,051,104 A | 4/2000 | Oriaran et al. |
| 6,068,731 A | 5/2000 | Dwiggins et al. |
| 6,096,169 A | 8/2000 | Hermans et al. |
| 6,103,063 A | 8/2000 | Oriaran et al. |
| 6,113,740 A | 9/2000 | Oriaran et al. |
| 6,120,642 A | 9/2000 | Lindsay et al. |
| 6,143,131 A | 11/2000 | Dwiggins et al. |
| 6,143,135 A | 11/2000 | Hada et al. |
| 6,153,053 A | 11/2000 | Harper et al. |
| 6,183,601 B1 | 2/2001 | Otto et al. |
| 6,197,154 B1 | 3/2001 | Chen et al. |
| 6,287,426 B1 | 9/2001 | Edwards et al. |
| 6,344,111 B1 * | 2/2002 | Wilhelm ............... 162/117 |

* cited by examiner

PAPER PRODUCT HAVING IMPROVED FUZZ-ON-EDGE PROPERTY

RELATED APPLICATIONS

The present application is based on a Provisional Application filed on May 12, 2000 having U.S. Application No. 60/204,083.

BACKGROUND OF THE INVENTION

Products made from base webs such as bath tissues, facial tissues, paper towels, industrial wipers, foodservice wipers, napkins, medical pads, and other similar products are designed to include several important properties. For example, the products should have a soft feel and, for most applications, should be highly absorbent. The products should also have good stretch characteristics and should resist tearing. Further, the products should also have good strength characteristics, should be abrasion resistant, and should not deteriorate in the environment in which they are used.

In the past, many attempts have been made to enhance and increase certain physical properties of such products. Unfortunately, however, when steps are taken to increase one property of these products, other characteristics of the products may be adversely affected. For instance, the softness of nonwoven products, such as various paper products, can be increased by several different methods, such as by selecting a particular fiber type, or by reducing cellulosic fiber bonding within the product. Increasing softness according to one of the above methods, however, may adversely affect the strength of the product. Conversely, steps normally taken to increase the strength of a fibrous web typically have an adverse impact upon the softness, the stiffness or the absorbency of the web.

The present invention is directed to improvements in base webs and to improvements in processes for making the webs in a manner that optimizes the physical properties of the webs. In particular, the present invention is directed to a process for improving the tactile properties, such as softness and stiffness, of base webs without severely diminishing the strength of the webs.

SUMMARY OF THE INVENTION

As stated above, the present invention is directed to further improvements in prior art constructions and methods, which are achieved by providing a process for producing base webs, namely base webs containing pulp fibers. The process includes the steps of first forming a base web. The base web can be made from various fibers and can be constructed in various ways. For instance, the base web can contain pulp fibers and/or staple fibers. Further, the base web can be formed in a wet-lay process, an air-forming process, or the like.

Once the base web is formed, the web is subjected to shear forces sufficient to improve the softness properties of the web. For instance, in one embodiment the web is placed in between a first moving conveyor and a second moving conveyor. The first and second moving conveyors are then guided around a shear-inducing roll while the base web is positioned in between the conveyors. The conveyors are sufficiently wrapped around the shear-inducing roll and are placed under a sufficient amount of tension so as to create shear forces that act upon the base web. The shear forces disrupt the web increasing the softness and decreasing the stiffness of the web. Of particular advantage, it has been discovered that the softness of the web is increased without substantially reducing the strength of the web. More particularly, it has been discovered that the process shifts the normal strength-softness curve so as to create webs having unique softness and strength properties.

When guided around the shear-inducing roll, the base web should have a moisture content of less than about 10%, particularly less than about 5%, and more particularly less than about 2%.

The shear-inducing roll can rotate or can be a stationary device. For most applications, the shear-inducing roll should have a small effective diameter, such as less than about 10 inches, particularly less than about 7 inches and more particularly from about 2 inches to about 6 inches. For most applications, the conveyors should be wrapped around the shear-inducing roll at least 30° and particularly from about 50° to about 270°. Further, the amount of tension placed upon the conveyors when wrapped around the shear-inducing roll should be at least 5 pounds per linear inch and particularly from about 10 pounds per linear inch to about 50 pounds per linear inch.

Various types of base webs can be processed according to the present invention. For example, in one embodiment, the base web can be a stratified web including a middle layer positioned between a first outer layer and a second outer layer. In one embodiment, the outer layers can have a tensile strength greater than the middle layer. For example, the outer layers can be made from softwood fibers, while the middle layer can be made from hardwood fibers.

Alternatively, the middle layer can have a tensile strength greater than the outer layers. It has been discovered by the present inventors that various unique products can be formed when using stratified base webs as described above.

The present inventors have discovered that the process of the present invention produces unique products having improved softness characteristics. In particular, it has been discovered that base webs made according to the present invention have improved void-volume properties and fuzz-on-edge properties. In this regard, the present invention is directed to a paper product that includes a nonwoven base web containing pulp fibers. The base web has a void volume greater than 12 g/g. Further, base webs made according to the present invention can have the above void-volume levels even at basis weights greater than 20 gsm, particularly greater than 25 gsm, and more particularly greater than 30 gsm.

The void volume properties of base webs made according to the present invention can also be improved without substantially decreasing the tensile strength of the webs. For example, base webs having a void volume greater than 12 g/g, can also have a geometric mean tensile strength of greater than about 170 g/in.

Besides dramatically improving the void volume of base webs, the process of the present invention also improves the fuzz-on-edge properties of the base web. In general, the fuzz-on-edge test measures the amount of fibers present on the surface of the web that are generally aligned in the z-direction. The degree of "fuzziness" of a web has also been measured in a test referred to as a "perimeter per edge length" test as described in European Application No. 0 539 703 which is incorporated herein by reference. A greater fuzz-on-edge generally indicates a softer web. It has been found that base webs made according to the present invention can have a fuzz-on-edge in an amount greater than 2.2 mm/mm, and particularly greater than 2.5 mm/mm.

Base webs having the above properties can be single-ply base webs made according to various processes. For example, in one embodiment, the base web can be an uncreped, through-air-dried base web. Alternatively, the base web can be dried on a yankee dryer and creped.

Base webs processed according to the present invention can have various applications and uses. In one particular embodiment, base webs made according to the present invention can be single ply base webs particularly well suited for use as a bath tissue. Beside bath tissues, however, the base webs can also be used and incorporated into facial tissues, paper towels, industrial wipers, foodservice wipers, napkins, medical pads, diapers, feminine-hygiene products, and other similar products.

Other features and aspects of the present invention are discussed in greater detail below.

BRIEF DESCRIPTION OF THE DRAWINGS

A full and enabling disclosure of the present invention, including the best mode thereof to one of ordinary skill in the art, is set forth more particularly in the remainder of the specification, including reference to the accompanying figures in which.

Figure 1:
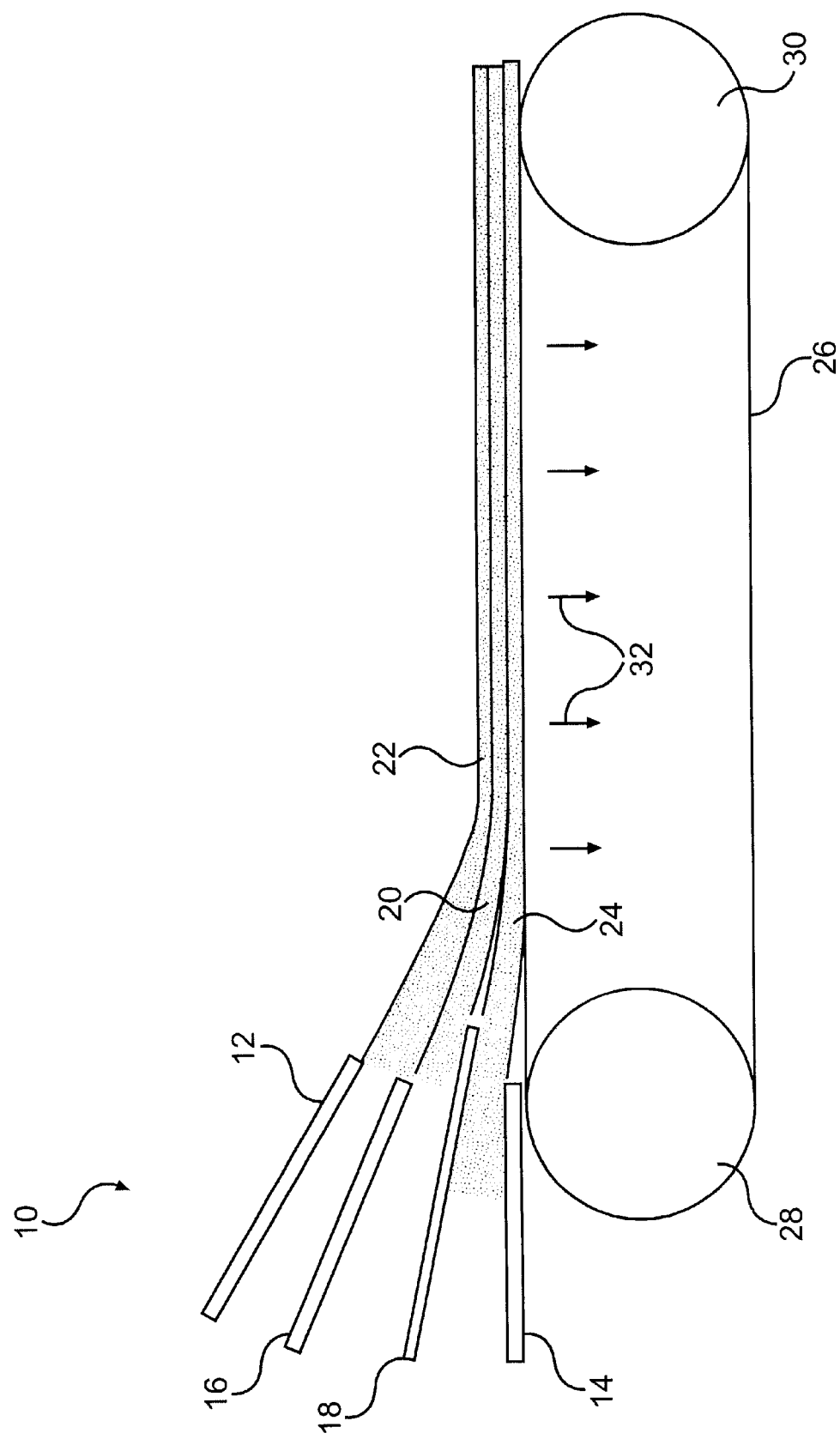
FIG. 1 is a schematic diagram of a fibrous web forming machine illustrating one embodiment for forming a base web having multiple layers in accordance with the present invention.

Repeat use of reference characters in the present specification and drawings is intended to represent same or analogous features or elements of the present invention.

DETAILED DESCRIPTION OF PREFERRED EMBODIMENTS

It is to be understood by one of ordinary skill in the art that the present discussion is a description of exemplary embodiments only, and is not intended as limiting the broader aspects of the present invention, which broader aspects are embodied in the exemplary construction.

In general, the present invention is directed to a process for improving the tactile properties of base webs without a subsequent substantial loss in tensile strength. The present invention is also directed to webs made from the process. In particular, the process of the present invention is well suited to increasing the softness and decreasing the stiffness of base webs, such as webs containing pulp fibers. Further, in some applications, the caliper of a web can be reduced while still gaining all of the above advantages.

Generally speaking, the process of the present invention includes the step of subjecting a previously formed base web to a shearing force in an amount sufficient to improve the softness of the web. For instance, the base web can be subjected to a shearing force in an amount sufficient to improve the void volume of the web and the fuzz-on-edge properties of the web.

In accordance with the present invention, a shearing force can be applied to the web by placing the web between a pair of moving conveyors. As used herein, a conveyor is intended to refer to a flexible sheet, such as a wire, a fabric, a felt, and the like. Once the base web is placed in between the moving conveyors, a speed differential is created between the two conveyors which applies a shearing force to the web. For example, in one embodiment, the conveyors can be guided around at least one shear-inducing element, such as a roll, while the web is sandwiched between the two conveyors. The shear-inducing element can rotate or can be stationary and typically has a small effective diameter, such as less than about 10 inches.

The moving conveyors have a sufficient amount of wrap around the shear-inducing element and are placed under sufficient tension to create shear forces that act upon the base web. Specifically, passing the conveyors over the shear-inducing element causes a speed differential in the conveyors which creates a shearing force that breaks bonds within the web or otherwise disrupts fiber entanglement within the web, where the web is weakest. Through this process, the softness of the web increases while the stiffness of the web is reduced. Unexpectedly, the present inventors have discovered that this softening occurs with substantially less loss of tensile strength than would be expected at the softness levels obtained.

Base webs that may be used in the process of the present invention can vary depending upon the particular application. In general, any suitable base web may be used in the process in order to improve the tactile properties of the web. Further, the webs can be made from any suitable type of fiber.

For example, the manner in which the base web of the present invention is formed may vary depending upon the particular application. In one embodiment, the web can contain pulp fibers and can be formed in a wet-lay process according to conventional paper making techniques. In a wet-lay process, the fiber furnish is combined with water to form an aqueous suspension. The aqueous suspension is spread onto a wire or felt and dried to form the web.

Alternatively, the base web of the present invention can be air formed. In this embodiment, air is used to transport the fibers and form a web. Air-forming processes are typically capable of processing longer fibers than most wet-lay processes, which may provide an advantage in some applications.

Figure 2:
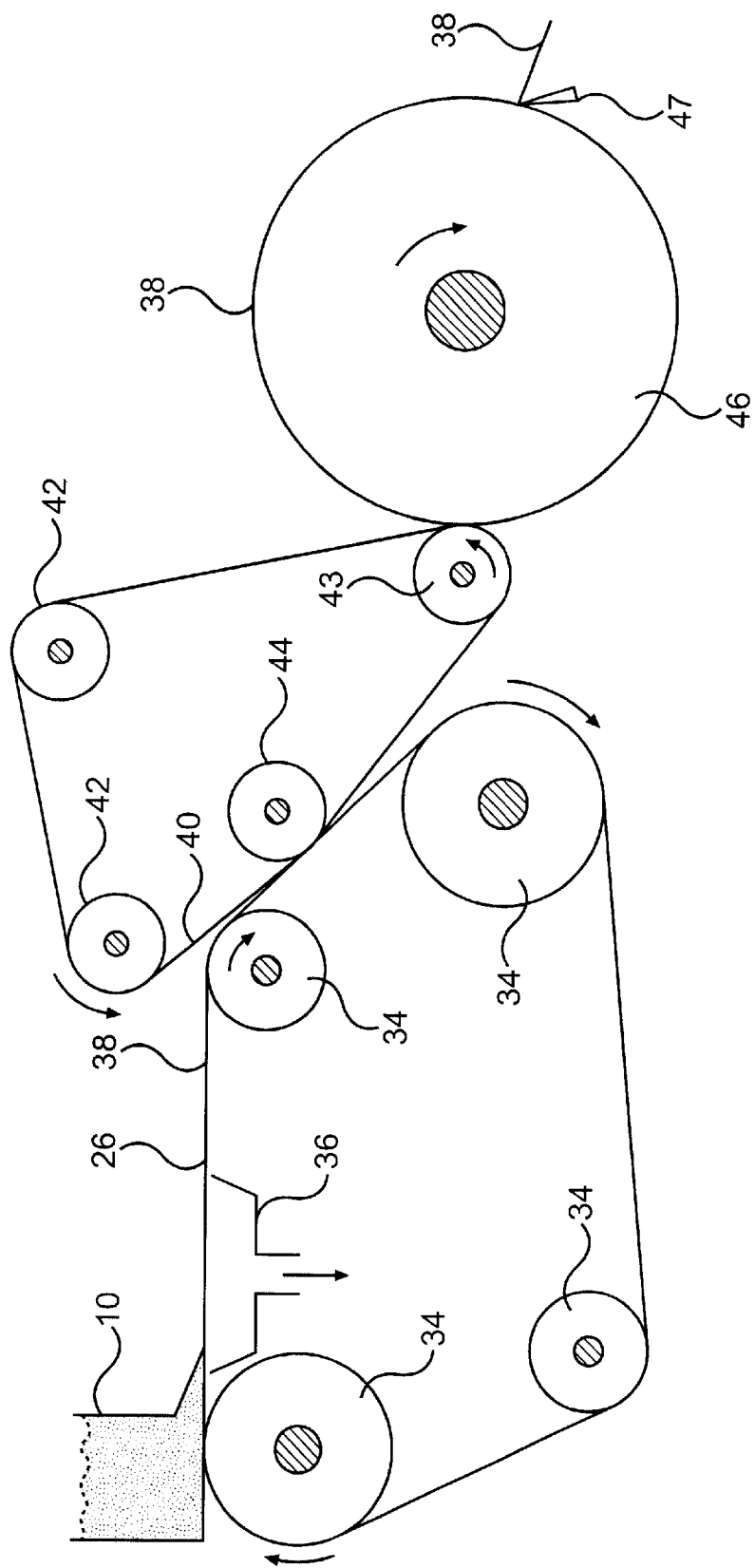
FIG. 2 is a schematic diagram of a fibrous web forming machine that crepes one side of the web.

Referring to FIG. 2, one embodiment of a process for producing a base web that may be used in accordance with the present invention is illustrated. The process illustrated in the figure depicts a wet-lay process, although, as described above, other techniques for forming the base web of the present invention may be used.

As shown in FIG. 2, the web-forming system includes a headbox 10 for receiving an aqueous suspension of fibers. Headbox 10 spreads the aqueous suspension of fibers onto a forming fabric 26 that is supported and driven by a plurality of guide rolls 34. A vacuum box 36 is disposed beneath forming fabric 26 and is adapted to remove water from the fiber furnish to assist in forming a web.

From forming fabric 26, a formed web 38 is transferred to a second fabric 40, which may be either a wire or a felt. Fabric 40 is supported for movement around a continuous path by a plurality of guide rolls 42. Also included is a pick up roll 44 designed to facilitate transfer of web 38 from fabric 26 to fabric 40. The speed at which fabric 40 can be driven is approximately the same speed at which fabric 26 is driven so that movement of web 38 through the system is consistent. Alternatively, the two fabrics can be run at different speeds, such as in a rush transfer process, in order to increase the bulk of the webs or for some other purpose.

From fabric 40, web 38, in this embodiment, is pressed onto the surface of a rotatable heated dryer drum 46, such as a Yankee dryer, by a press roll 43. Web 38 is lightly pressed into engagement with the surface of dryer drum 46 to which it adheres, due to its moisture content and its preference for the smoother of the two surfaces. As web 38 is carried through a portion of the rotational path of the dryer surface, heat is imparted to the web causing most of the moisture contained within the web to be evaporated.

Web 38 is then removed from dryer drum 46 by a creping blade 47. Creping web 38 as it is formed reduces internal bonding within the web and increases softness.

In an alternative embodiment, instead of wet pressing the base web 38 onto a dryer drum and creping the web, the web can be through-air dried. A through-air dryer accomplishes the removal of moisture from the base web by passing air through the web without applying any mechanical pressure.

Figure 3:
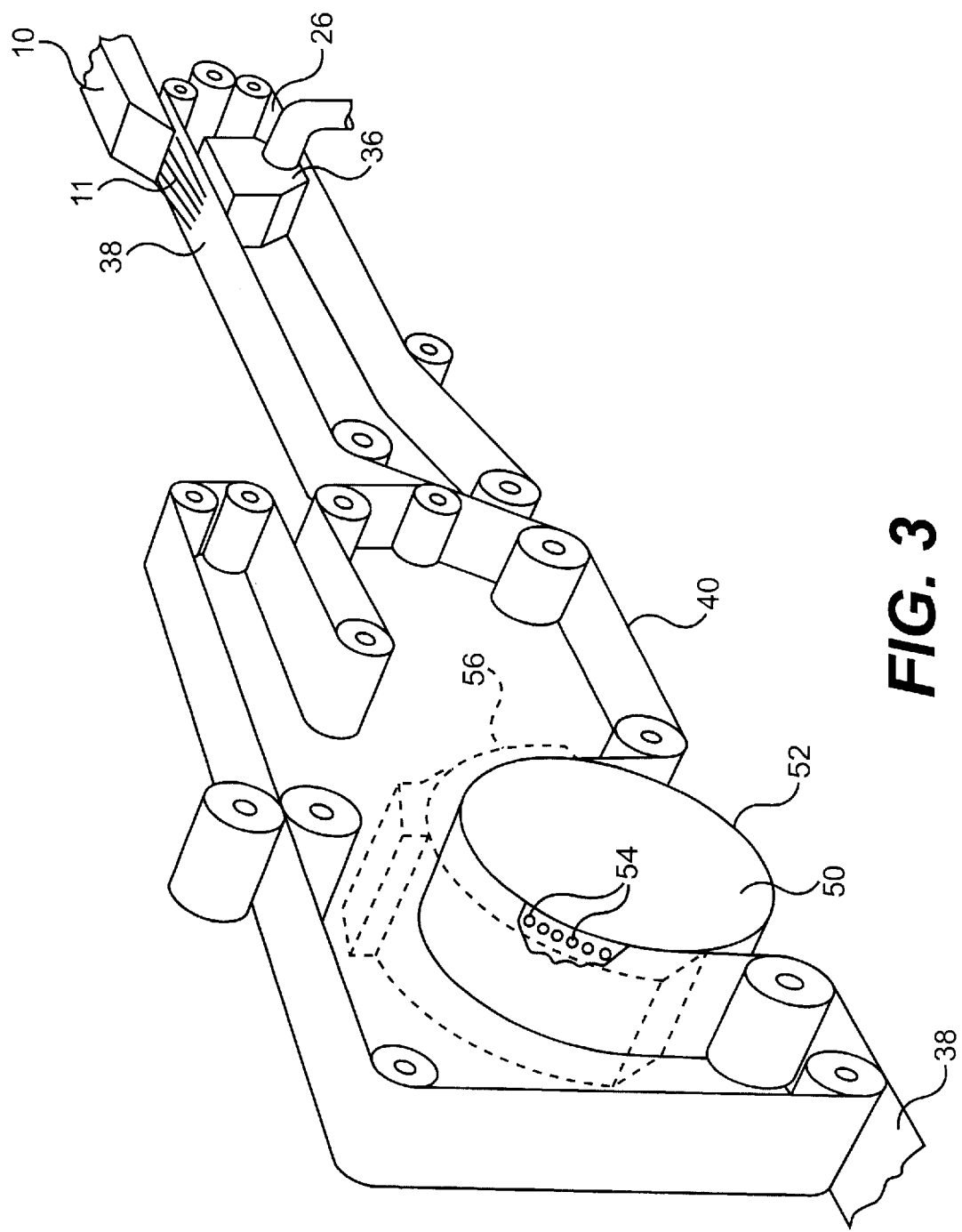
FIG. 3 is a perspective view with cut away portions of a fibrous web forming machine that includes a through-air dryer for removing moisture from the web.

For example, referring to FIG. 3, an alternative embodiment for forming a base web for use in the process of the present invention containing a through-air dryer is illustrated. As shown, a dilute aqueous suspension of fibers is supplied by a headbox 10 and deposited via a sluice 11 in uniform dispersion onto a forming fabric 26 in order to form a base web 38.

Once deposited onto the forming fabric 26, water is removed from the web 38 by combinations of gravity, centrifugal force and vacuum suction depending upon the forming configuration. As shown in this embodiment, and similar to FIG. 2, a vacuum box 36 can be disposed beneath the forming fabric 26 for removing water and facilitating formation of the web 38.

From the forming fabric 26, the base web 38 is then transferred to a second fabric 40. The second fabric 40 carries the web through a through-air drying apparatus 50. The through-air dryer 50 dries the base web 38 without applying a compressive force in order to maximize bulk. For example, as shown in FIG. 3, the through-air drying apparatus 50 includes an outer rotatable cylinder 52 with perforations 54 in combination with an outer hood 56. Specifically, the fabric 40 carries the web 38 over the upper portion of the through air drying apparatus outer cylinder 52. Heated air is drawn through perforations 54 which contacts the web 38 and removes moisture. In one embodiment, the temperature of the heated air forced through the perforations 54 can be from about 170° F. to about 500° F.

Figure 4:
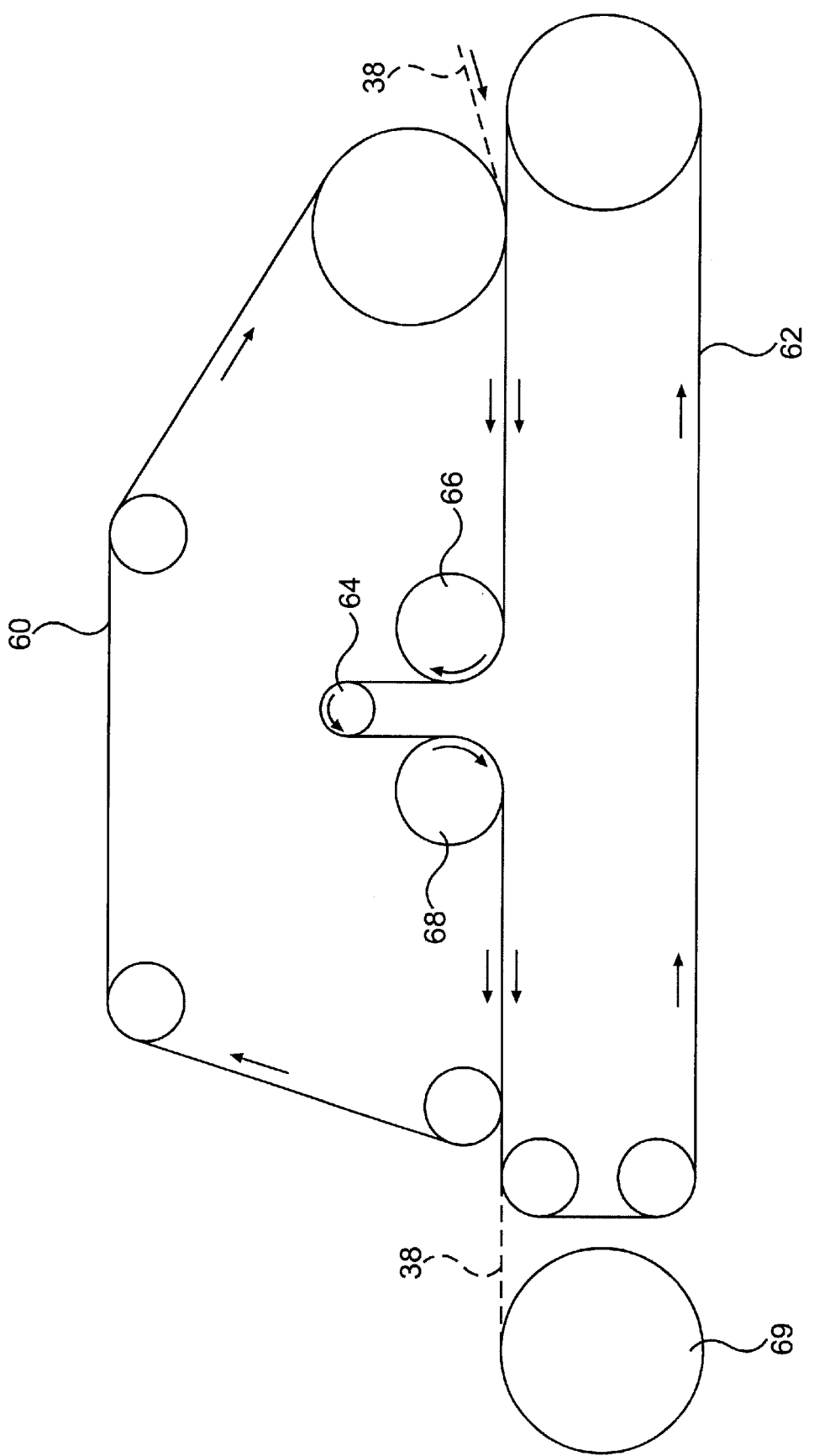
FIG. 4 is a schematic diagram of one embodiment for a process for improving the tactile properties of a formed base web in accordance with the present invention.

After the base web 38 is formed, such as through one of the processes illustrated in FIGS. 2 and 3 or any other suitable process, the web is placed between a pair of moving conveyors and pressed around a shear-inducing element in accordance with the present invention. For instance, one embodiment of a process for improving the tactile properties of a base web in accordance with the present invention is illustrated in FIG. 4. As shown, the base web 38 is supplied between a first moving conveyor 60 and a second moving conveyor 62. The speed at which the conveyors 60 and 62 are moving is generally not critical to the present invention. For most commercial applications, the conveyors can be moving at a speed of from about 1,000 feet per minute to about 6,000 feet per minute.

Once positioned in between the first conveyor 60 and the second conveyor 62, the base web and the conveyors are guided around a shear-inducing roll 64 by a pair of support rolls 66 and 68. In accordance with the present invention, the conveyors 60 and 62 are placed under tension and are wrapped around the shear-inducing roll 64 in amounts sufficient to create shear forces that act upon the base web 38. In particular, when the conveyors are passed over the shear-inducing roll, a speed differential develops in the conveyors.

Due to the interaction between the surfaces of the conveyors and the contacting surface of the web, the speed differential of the conveyors can be translated into a speed differential between the two web surfaces. Factors which can affect the web surface/conveyor surface interaction can include but are not limited to, for example, the coefficient of friction at the conveyor surfaces, the tension of the conveyors, and the moisture content of the web. A speed differential between the two web surfaces can create shearing forces which act upon the base web. The shearing forces can break bonds within the web where the web is weakest, which subsequently increases the softness and decreases the stiffness of the web.

Further, the present inventors have discovered that these improvements are realized without a significant decrease in tensile strength as normally occurs in other processes designed to increase softness.

The inventors have also unexpectedly discovered that the process of the present invention produces a web with distinct properties. Specifically, the web produced by the present invention shows improved characteristics in terms of both void volume and fuzz-on-edge properties. Of particular significance, it is believed that void-volume and fuzz-on-edge characteristics are completely unrelated properties. Thus, it is believed that the shearing force applied to the base web according to the present invention is improving two unrelated properties that translate into greater softness.

In general, void volume is a measure of the volume of liquid which can be contained within a sheet. As used herein, void volume is determined according to the POROFIL test described in EXAMPLE 2 below. It is generally held that an increase in void volume becomes more difficult as basis weight of the sheet increases, due primarily to surface effects of higher basis weight webs. The webs produced by the present invention have unexpectedly been found to have a void volume greater than 11.5 g/g and particularly greater than 12 g/g. This result is even more unexpected due to the relatively high basis weight tissue webs which can be produced in certain embodiments of the present invention. For example, in one embodiment of the present invention, single-ply webs can be produced having a basis weight of greater than about 20 gsm and a void volume of greater than 11.5 g/g. More specifically, a single-ply web, suitable as a bath tissue, can be produced by the present invention that can have a basis weight of more than about 30 gsm and a void volume of greater than about 12.0 g/g.

An increase in void volume has been correlated with an increase in softness of a sheet, as in, for example, U.S. Pat. No. 5,494,554 and EP 0 613 979 A1 both to Edwards et al., both of which are incorporated in their entirety by reference thereto.

As stated above, besides void volume, the process of the present invention also increases the fuzz-on-edge properties of the base web. As used herein, a fuzz-on-edge test is a test that generally measures the amount of fibers present on the surface of the base web that protrude from the sheet. As used herein, the fuzz-on-edge is measured according to the test as described in EXAMPLE 2 below. The greater the fuzz-on-edge of a base web, the softer the base web feels. In particular, the fuzz-on-edge corresponds to a greater number of fibers on the surface of the web in the z-direction which provides a "fuzzy" soft feel.

Base webs made according to the present invention can have a fuzz-on-edge in an amount greater than about 2.0 mm/mm, particularly greater than 2.2 mm/mm, and more particularly greater than about 2.5 mm/mm.

Referring back to FIG. 4, when fed around the shear-inducing roll 64, base web 38 should generally have a low moisture content. For example, the base web 38 should have a moisture content of less than about 10% by weight, particularly less than about 5% by weight, and more particularly less than about 2% by weight.

As shown in FIG. 4, the shear-inducing roll 64 can be a rotating roll having a relatively small diameter. In other embodiments, however, the shear-inducing roll can be a stationary roll. The effective diameter of the shear-inducing roll, for most applications, should be less than about 10 inches, particularly less than about 7 inches, and more particularly from about 2 inches to about six inches.

The amount that conveyors 60 and 62 are wrapped around the shear-inducing roll 64 can vary depending upon the particular application and the amount of shear that is desired to be exerted on the web. For most applications, however, the conveyors should be wrapped around the shear-inducing roll in an amount from about 30° to about 270°, particularly from about 50° to about 200°, and more particularly from about 80° to about 180°. In the embodiment illustrated in FIG. 4, the amount of wrap placed around the shear-inducing roll can be adjusted by adjusting the position of either the shear-inducing roll 64 or the support rolls 66 and 68. For instance, by moving the shear-inducing roll 64 down closer to the support rolls 66 and 68, the conveyors will wrap around the shear-inducing roll 64 a lesser extent.

As described above, besides the amount of wrap that is placed around the shear-inducing roll, the amount of tension placed upon the conveyors 60 and 62 can also have an impact on the amount of shear that is exerted on the base web 38. The amount of tension placed upon the conveyors will depend upon the particular application. For most applications, however, the conveyors 60 and 62 should be placed under tension in an amount from about 5 pounds per linear inch to about 90 pounds per linear inch, particularly from about 10 pounds per linear inch to about 50 pounds per linear inch, and more particularly from about 30 pounds per linear inch to about 40 pounds per linear inch.

As described above, when the conveyors 60 and 62 are wrapped around the shear-inducing roll 64 under a sufficient amount of tension, a surface speed differential develops between the two surfaces of the web that creates the shear forces. For most applications, the speed differential should be from about 0.5% to about 5%, and particularly from about 1% to about 3% with conveyor on the outside moving faster than the conveyor contacting the roll.

After the base web 38 has been guided around the shear-inducing roll 64, the web can be further processed as desired. In one embodiment, as shown in FIG. 4, the web can be collected onto a reel 69 for later packaging.

During this process, the tactile properties of the base web can be greatly enhanced, without seriously affecting the strength of the web. Further, in some applications, it has been discovered that the caliper of the web can be dramatically reduced. Caliper reduction without adversely affecting other properties of the web is beneficial in that more material can be placed upon reel 69, which provides various processing benefits. The amount of caliper reduction for a given base web will depend upon the application. In general, the caliper of a sheet is reduced by the pressure (P) applied to it by the tension (T) of the fabrics and the radius (R) of the roll, governed by the equation P=T/R.

The amount of caliper reduction achieved can be controlled by adjusting numerous variables. The number of shear-inducing rolls, the radius of the rolls, dwell time within the nip, nip pressure, conveyor type and base sheet structure all have an impact on the amount of caliper the process can remove. Percent caliper reduction increases with an increase in dwell time, number of rolls, nip pressure, and fabric mesh. Dwell time can be affected by the secondary variables of speed and wrap angle. Nip pressure can be varied by the secondary variables of fabric tension and roll diameter. Fabric mesh can be varied by using fabrics of differing knuckle surfaces. Thus far, it has been discovered that the caliper of a base web can be decreased up to as much as 75%, and particularly from about 20% to about 70%.

Figure 5:
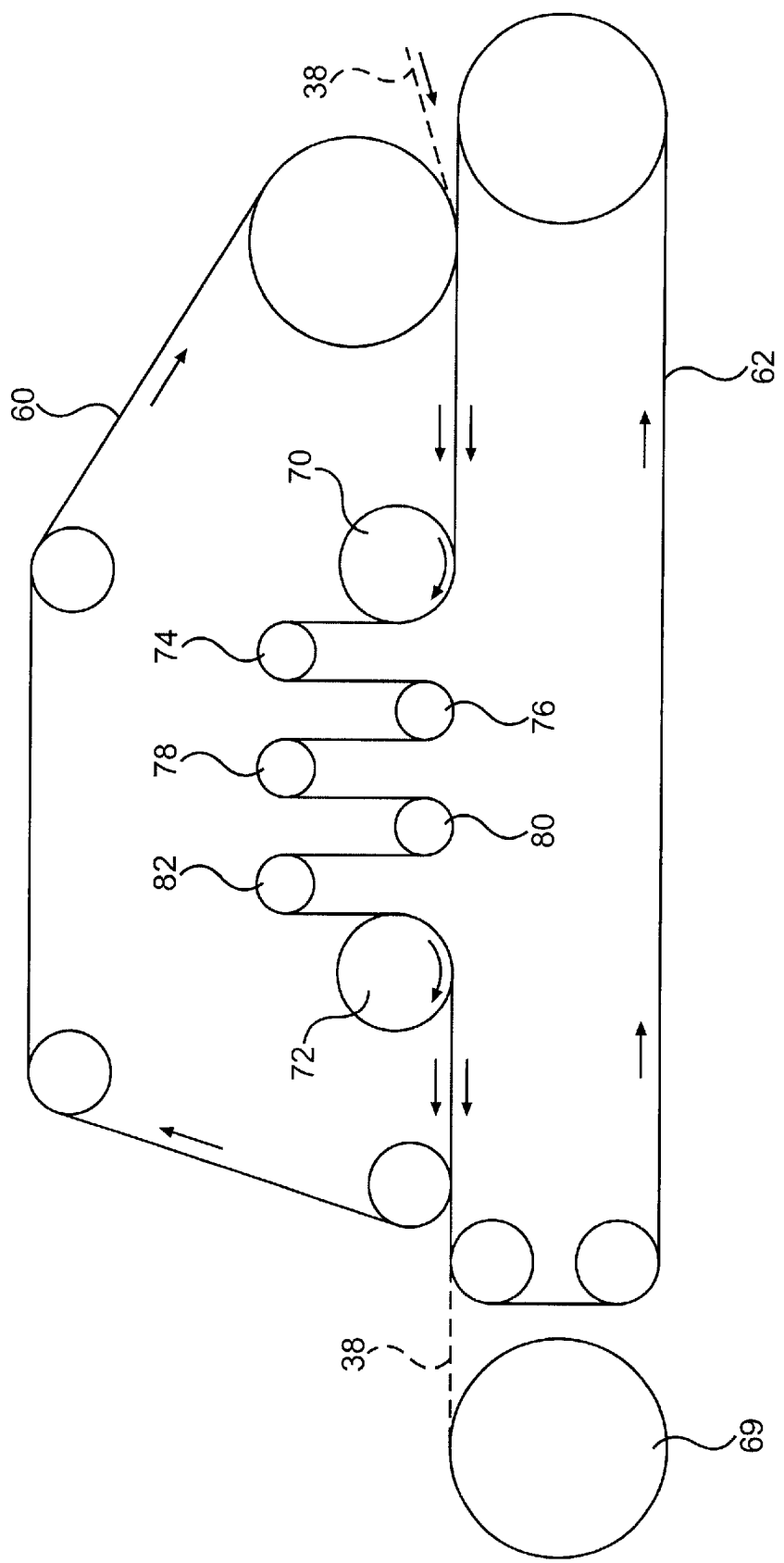
FIG. 5 is a schematic diagram of an alternative embodiment of a process for improving the tactile properties of a formed base web made in accordance with the present invention.

In the embodiment illustrated in FIG. 4, the system includes a single shear-inducing roll 64. In other embodiments, however, more shear-inducing rolls can be used. For instance, in other embodiments, the conveyors can be wrapped around two shear-inducing rolls, three shear-inducing rolls, and even up to ten shear-inducing rolls. Referring to FIG. 5, an alternative embodiment of the present invention is illustrated that includes five shear-inducing rolls.

As shown, the base web 38 is fed between the first conveyor 60 and the second conveyor 62 and is then wrapped around support rolls 70 and 72 and shear-inducing rolls 74, 76, 78, 80, and 82. In general, using more shear-inducing rolls can create more shear that is exerted on the base web. Although the shear-inducing rolls are illustrated as having approximately equal diameters, alternative embodiments may be desired with some or all of the shear-inducing rolls having diameters which are unequal to the others.

When using more than one shear-inducing roll, the total wrap of the conveyors around all of the shear-inducing rolls should be at least 90° for most embodiments. More particularly, especially when using more than two shear-inducing rolls, the total wrap should be greater than 100°, and particularly greater than 120°. The total wrap, however, can increase or decrease depending upon increasing or decreasing the number of shear-inducing rolls respectively.

Figure 6:
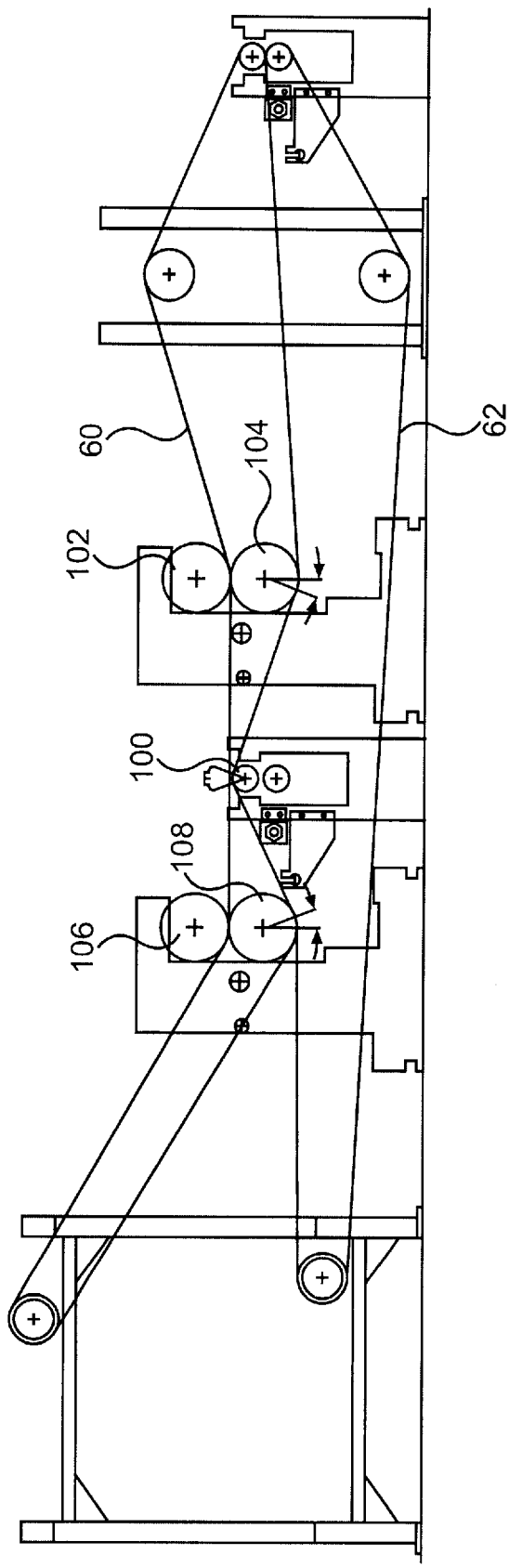
FIG. 6 is a schematic diagram of another alternative embodiment of a process for improving the tactile properties of a formed base web made in accordance with the present invention.
Figure 7:
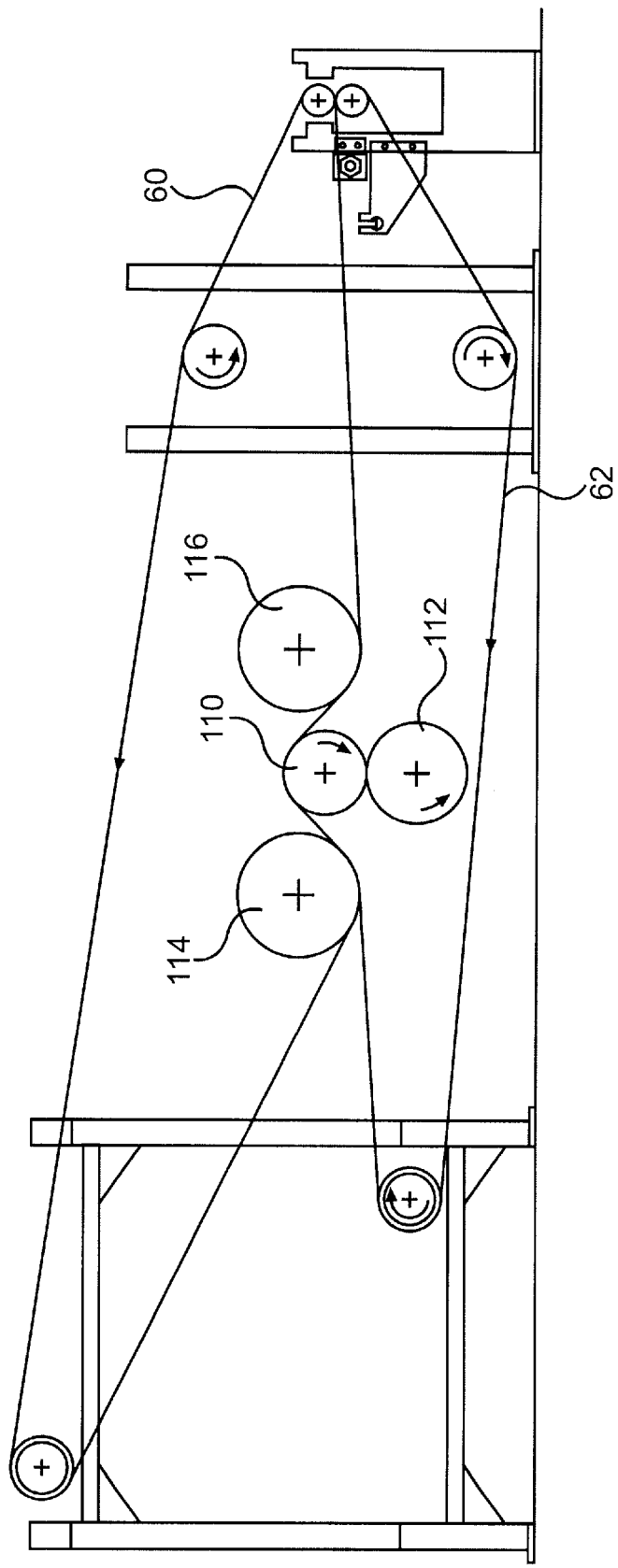
FIG. 7 is a schematic diagram of a further alternative embodiment of a process for improving the tactile properties of a formed base web made in accordance with the present invention.

Further embodiments of systems made in accordance with the present invention are illustrated in FIGS. 6 and 7. The system illustrated in FIG. 6 includes a single shear-inducing roll 100. As shown, conveyors 60 and 62 are guided around the shear-inducing roll 100 by support rolls 102, 104, 106 and 108.

The system illustrated in FIG. 7 also includes a single shear-inducing roll 110. It should be understood, however, that more shear-inducing rolls can be included in any of the systems illustrated. As shown in FIG. 7, shear-inducing roll 110 is supported by a backing roll 112. In order to facilitate the amount of wrap around shear-inducing roll 110, the system further includes support rolls 114 and 116.

As stated above, base webs processed according to the present invention can be made from various materials and fibers. For instance, the base web can be made from pulp fibers, other natural fibers, synthetic fibers, and the like.

For instance, in one embodiment of the present invention, the base web contains pulp fibers either alone or in combination with other types of fibers. The pulp fibers used in forming the web can be, for instance, softwood fibers having an average fiber length of greater than 1 mm and particularly from about 2 to 5 mm based on a length weighted average. Such fibers can include Northern softwood kraft fibers. Secondary fibers obtained from recycled materials may also be used.

In one embodiment, staple fibers (and filaments) can be added to the web to increase the strength, bulk, softness and smoothness of the web. Staple fibers can include, for instance, polyolefin fibers, polyester fibers, nylon fibers, polyvinyl acetate fibers, cotton fibers, rayon fibers, non-woody plant fibers, and mixtures thereof. In general, staple fibers are typically longer than pulp fibers. For instance, staple fibers typically have fiber lengths of 5 mm and greater.

The staple fibers added to the base web can also include bicomponent fibers. Bicomponent fibers are fibers that can contain two materials such as, but not limited to, in a side by side arrangement or in a core and sheath arrangement. In a core and sheath fiber, generally the sheath polymer has a lower melting temperature than the core polymer. For instance, the core polymer, in one embodiment, can be nylon or a polyester, while the sheath polymer can be a polyolefin such as polyethylene or polypropylene. Such commercially available bicomponent fibers include CELBOND fibers marketed by the Hoechst Celanese Company.

The staple fibers used in the base web of the present invention can also be curled or crimped. The fibers can be curled or crimped, for instance, by adding a chemical agent to the fibers or subjecting the fibers to a mechanical process. Curled or crimped fibers may create more entanglement and void volume within the web and further increase the amount of fibers oriented in the Z direction as well as increase web strength properties.

In one embodiment, when forming paper products containing pulp fibers, the staple fibers can be added to the web in an amount from about 5% to about 30% by weight and particularly from about 5% to about 20% by weight.

When the base web of the present invention is not used to make paper products, but instead is incorporated into other products such as diapers, feminine-hygiene products, garments, personal-care products, and various other products, the base web can be made from greater amounts of staple fibers.

Besides pulp fibers and staple fibers, thermomechanical pulp can also be added to the base web. Thermomechanical pulp, as is known to one skilled in the art, refers to pulp that is not cooked during the pulping process to the same extent as conventional pulps. Thermomechanical pulp tends to contain stiff fibers and has higher levels of lignin. Thermomechanical pulp can be added to the base web of the present invention in order to create an open pore structure, thus increasing bulk and absorbency and improving resistance to wet collapse.

When present, the thermomechanical pulp can be added to the base web in an amount from about 10% to about 30% by weight. When using thermomechanical pulp, a wetting agent is also preferably added during formation of the web. The wetting agent can be added in an amount less than about 1% and, in one embodiment, can be a sulphonated glycol.

In some embodiments, it is desirable to limit the amount of inner fiber-to-fiber bond strength. In this regard, the fiber furnish used to form the base web can be treated with a chemical debonding agent. The debonding agent can be added to the fiber slurry during the pulping process or can be added directly into the headbox. Suitable debonding agents that may be used in the present invention include cationic debonding agents such as fatty dialkyl quaternary amine salts, mono fatty alkyl tertiary amine salts, primary amine salts, imidazoline quaternary salts, and unsaturated fatty alkyl amine salts. Other suitable debonding agents are disclosed in U.S. Pat. No. 5,529,665 to Kaun which is incorporated herein by reference.

In one embodiment, the debonding agent used in the process of the present invention can be an organic quaternary ammonium chloride. In this embodiment, the debonding agent can be added to the fiber slurry in an amount from about 0.1% to about 1% by weight, based on the total weight of fibers present within the slurry.

The base web of the present invention may also have a multi-layer construction. For instance, the web can be made from a stratified fiber furnish having at least three principal layers.

It has been discovered by the present inventors that various unique products can be formed when processing a stratified base web according to the present invention. For example, as described above, the process of the present invention causes web disruption in the area of the web that is weakest. Consequently, one particular embodiment of the present invention is directed to using a stratified base web that contains weak outer layers and a strong center layer. Upon exposure to the shear forces created through the process of the present invention, bonds are broken on the outer surface of the sheet, while the strength of the center layer is maintained. The net effect is a base web having improved softness and stiffness with minimal strength loss.

In an alternative embodiment, a stratified base web can be used that has outer layers having a greater tensile strength than a middle layer. In this embodiment, upon exposure to the shear forces created by the process of the present invention, bonds in the middle layer fail but the integrity of the outer layers is maintained. The resulting sheet simulates, in some respects, the properties of a two-ply sheet.

There are various methods available for creating stratified base webs. For instance, referring to FIG. 1, one embodiment of a device for forming a multi-layered stratified fiber furnish is illustrated. As shown, a three-layered headbox generally 10may include an upper headbox wall 12 and a lower headbox wall 14. Headbox 10 may further include a first divider 16 and a second divider 18, which separate three fiber stock layers. Each of the fiber layers 24, 20, and 22 comprise a dilute aqueous suspension of fibers.

An endless traveling forming fabric 26, suitably supported and driven by rolls 28 and 30, receives the layered stock issuing from headbox 10. Once retained on fabric 26, the layered fiber suspension passes water through the fabric as shown by the arrows 32. Water removal is achieved by combinations of gravity, centrifugal force and vacuum suction depending on the forming configuration.

Forming multi-layered webs is also described and disclosed in U.S. Pat. No. 5,129,988 to Farrington. Jr. and in U.S. Pat. No. 5,494,554 to Edwards, et al., which are both incorporated herein by reference.

In forming stratified base webs, various methods and techniques are available for creating layers that have different tensile strengths. For example, debonding agents can be used as described above in order to alter the strength of a particular layer.

Alternatively, different fiber furnishes can be used for each layer in order to create a layer with desired characteristics. For example, in one embodiment, softwood fibers can be incorporated into a layer for providing tensile strength, while hardwood fibers can be incorporated into an adjacent layer for creating a weaker tensile strength layer.

More particularly, it is known that layers containing hardwood fibers typically have a lower tensile strength than layers containing softwood fibers. Hardwood fibers have a relatively short fiber length. For instance, hardwood fibers can have a length of less than about 2 millimeters and particularly less than about 1.5 millimeters.

In one embodiment, the hardwood fibers incorporated into a layer of the base web include eucalyptus fibers. Eucalyptus fibers typically have a length of from about 0.8 millimeters to about 1.2 millimeters. When added to the web, eucalyptus fibers increase the softness, enhance the brightness, increase the opacity, and increase the wicking ability of the web.

Besides eucalyptus fibers, other hardwood fibers may also be incorporated into the base web of the present invention. Such fibers include, for instance, maple fibers, birch fibers and possibly recycled hardwood fibers.

In general, the above-described hardwood fibers can be present in the base web in any suitable amount. For example, the fibers can comprise from about 5% to about 100% by weight of one layer of the web.

The hardwood fibers can be present within the lower tensile strength layer of the web either alone or in combination with other fibers, such as other cellulosic fibers. For instance, the hardwood fibers can be combined with softwood fibers, with superabsorbent materials, and with thermomechanical pulp.

As described above, stronger tensile strength layers can be formed using softwood fibers, especially when adjacent weaker tensile strength layers are made from hardwood fibers. The softwood fibers can be present alone or in combination with other fibers. For instance, in some embodiments, staple fibers, such as synthetic fibers, can be combined with the softwood fibers.

The weight of each layer of a stratified base web in relation to the total weight of the web is generally not critical. In most embodiments, however, the weight of each outer layer will be from about 15% to about 40% of the total weight of the web, and particularly from about 25% to about 35% of the weight of the web.

The basis weight of base webs made according to the present invention can vary depending upon the particular application. In general, for most applications, the basis weight can be from about 5 pounds per 2,880 square feet (ream) (8.5 gsm) to about 80 pounds per ream (136 gsm), and particularly from about 6 pounds per ream (10.2 gsm) to about 30 pounds per ream (51 gsm). In one embodiment, the present invention can be used to construct a single ply bath tissue having a basis weight of from about 20 gsm to about 40 gsm. Some other uses of the base webs include use as a wiping product, as a napkin, as a medical pad, as an absorbent layer in a laminate product, as a placemat, as a drop cloth, as a cover material, as a facial tissue, or for any product that requires liquid absorbency.

The present invention may be better understood with reference to the following examples.

EXAMPLE 1

In this experiment, paper webs were produced, placed between two fabrics, and then guided around at least one shear-inducing roll. More particularly, stratified webs were tested which included three layers. The two outer layers of the web were made from eucalyptus fibers. The middle layer, however, contained softwood fibers. The webs were produced using a through-air dryer similar to the system illustrated in FIG. 3. The base webs had an average basis weight of about 18.9 lbs/ream.

Once formed, the webs were then placed in between a pair of fabrics and guided around at least one shear-inducing roll, similar to the configuration illustrated in FIG. 4.

In the first set of experiments, the base webs were wrapped around 3 shear-inducing rolls at a pressure of 25 pounds per linear inch. The fabrics were wrapped around the shear-inducing rolls in an amount of about 45°.

During the first set of tests, the diameter of the shear-inducing rolls was varied between 2 inches, 4.5 inches and 10.5 inches. Further, the amount of softwood fibers contained in the web was also varied (middle layer of the web) from 28% by weight to 31% by weight.

Figure 8:
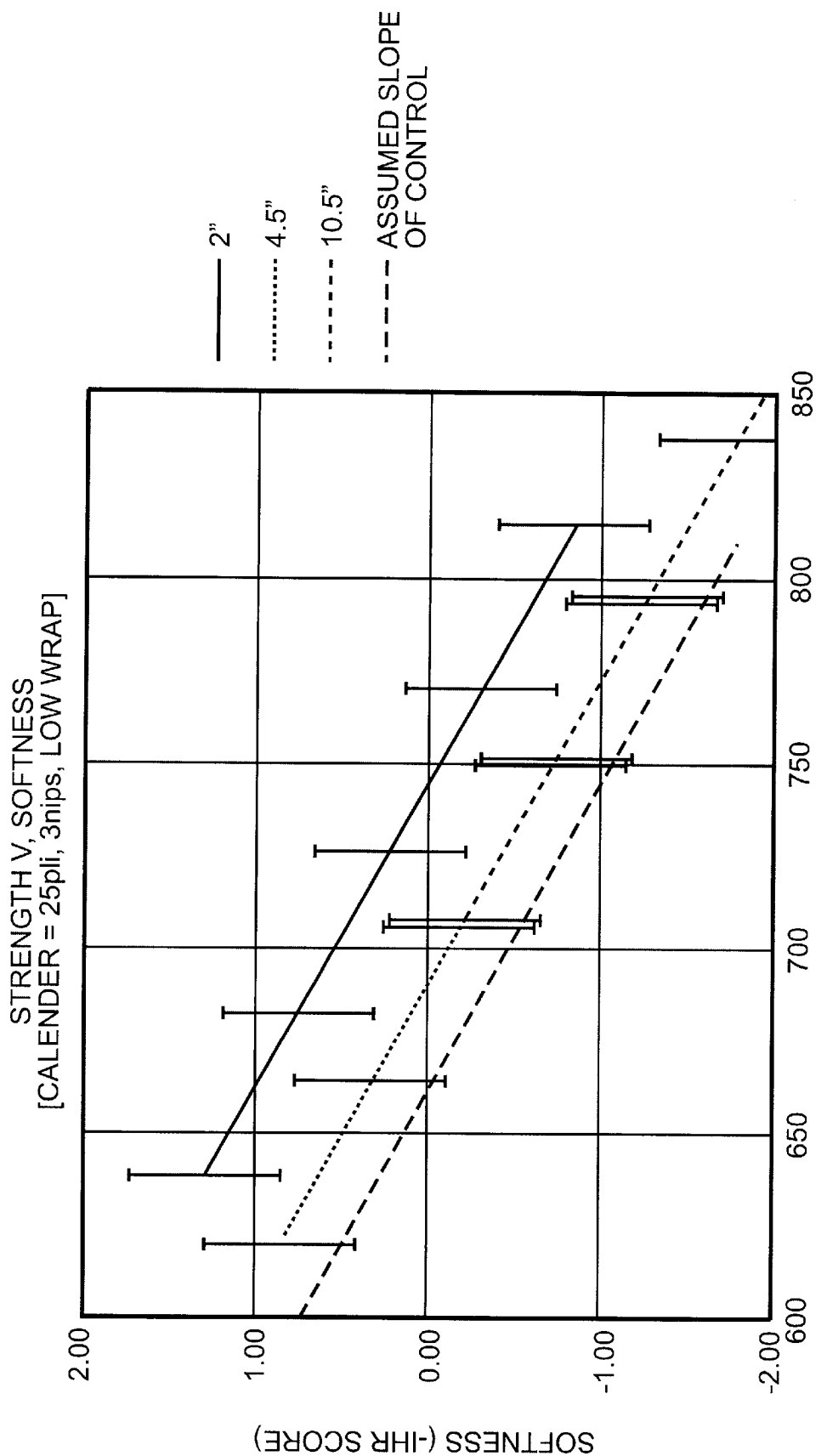
FIGS. 8 and 9 are the results obtained in the example described below.

Linear regression mathematical models were developed for strength and softness in order to create strength and softness curves. The results of the first set of experiments is illustrated in FIG. 8. For purposes of comparison, a control curve was also created. The control curve was produced by calendering the base web at a pressure of 150 pounds per linear inch, instead of subjecting the web to the shear-inducing rolls and then estimating a curve.

During these tests, softness was determined using an in hand ranking test (IHR). Panelists received 6 samples and were asked to rank them for softness based upon subjective criteria. Specifically, the panelists received different sets of samples several times. Each sample was coded. Replicates were compared in order to estimate error. The panelists response data was modeled with Logistic Regression to determine paired scores and log odds.

Strength was determined using a geometric mean tensile strength test (GMT). In particular, the tensile strength of samples was determined in the machine direction and in the cross machine direction. The size of the samples tested were 3 inches in width unless indicated to the contrary. During the test, each end of a sample was placed in an opposing clamp. The clamps held the material in the same plane and moved apart at a ten inch per minute rate of extension. The clamps moved apart until breakage occurred in order to measure the tensile strength of the sample. The geometric mean tensile strength is then calculated by taking the square root of the machine-direction tensile strength of the sample multiplied by the cross-direction tensile strength of the sample.

Tensile strength tests can be performed, for instance, on the Sintech 2 tester, available from the Sintech Corporation of Cary, N.C., the Instron Model™ available from the Instron Corporation of Canton, Mass., a Thwing-Albert Model INTELLECT II available from the Thwing-Albert Instrument Company of Philadelphia., Pa., or SYNERGY 100 available from MTS Systems, Corp. located in Eden Prairie, Minn. Results are reported in grams or in grams per inch width of sample.

In order to construct the graph illustrated in FIG. 8, linear regression models were calculated for strength and softness. Specifically, a Y=f (x) model for strength and softness was created. A spreadsheet was created listing softness and strength values as the percent of softwood in the web varied for each of the three roll diameters of interest (2 inches, 4.5 inches, and 10.5 inches). For each point in the spreadsheet a value for strength and softness was calculated from the regression models. The graph shown in FIG. 8 was then created plotting softness on one axis and strength on the other axis grouped by the roll diameter.

As shown in FIG. 8 the process of the present invention shifts the strength/softness curve towards creating softer and stronger webs. Further, decreasing the shear-inducing roll diameter further increases the softness of the webs at a given strength.

During the experiments, it was also noticed that between 5% to 15% caliper reduction was obtained, without positively or negatively affecting any other product attributes.

Figure 9:
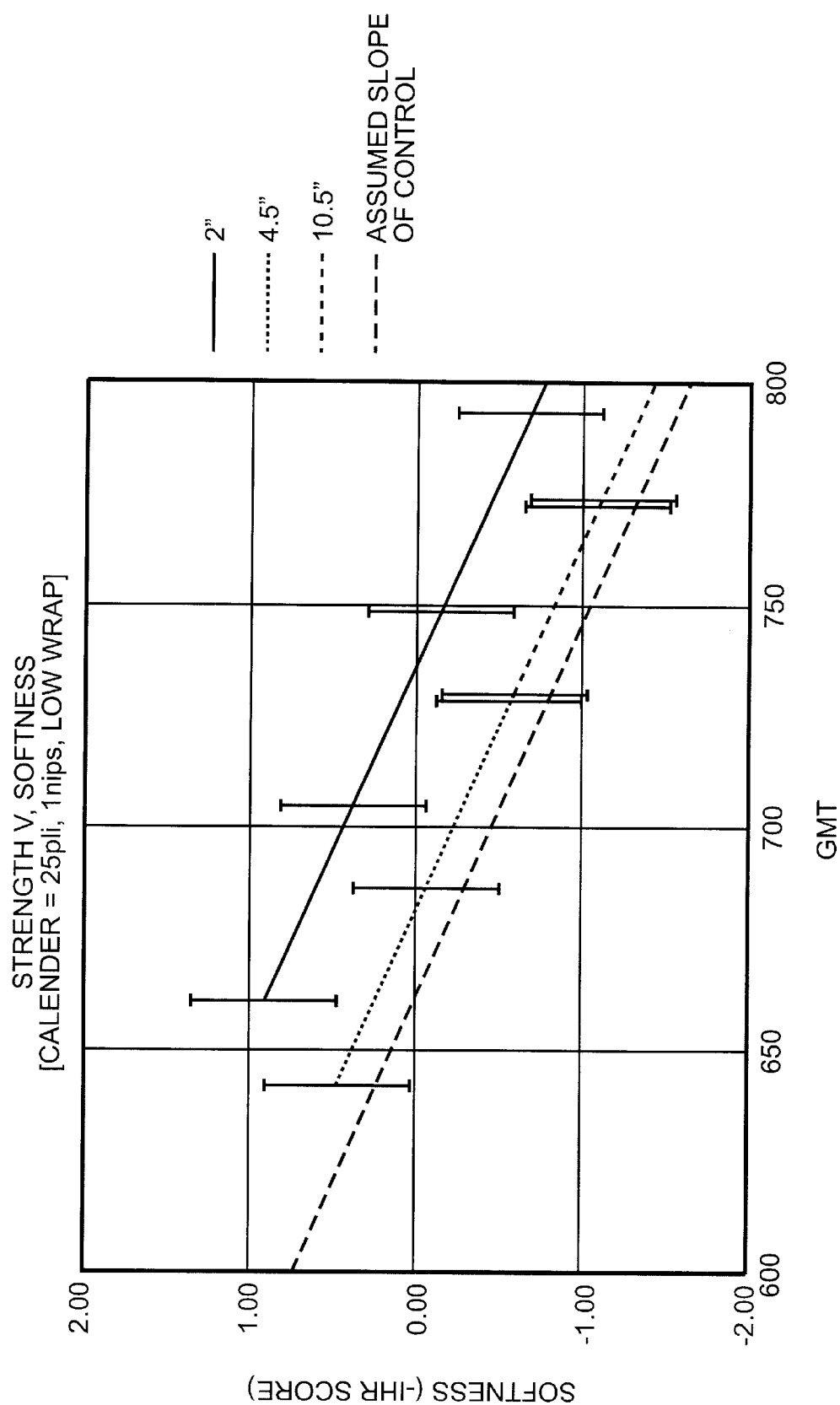

Using the mathematical models, another set of curves was generated from another set of experiments. Specifically, in this set of experiments, only a single shear-inducing roll was used. The results are shown in FIG. 9.

As shown, a decrease in the diameter of the shear-inducing roll had a greater impact upon the base webs in comparison to the control.

EXAMPLE 2

In this experiment, a nonwoven web was formed, placed between two conveyors, and then guided around three small rolls. The web produced was a stratified web including three layers. The center layer was 100% softwood and made up approximately 34% by weight of the total web. The two outer layers were each approximately 33% by weight of the web and were a 3:1 mixture (by weight) of eucalyptus fibers and broke. In addition, 5.1 kg/metric ton of total fiber furnish of PROSOFT TQ 1003 debonder obtained from Hercules, Inc. was added to the outer layers of the web and 6.0 kg/metric ton of total fiber furnish of HERCOBOND wet strength agent obtained from Hercules, Inc. was added to the center layer. Additionally, the softwood fibers were refined at a load of 2.75 HP-day/metric ton.

The web was produced using a through-air dryer apparatus similar to the system illustrated in FIG. 3. The through-air drying apparatus included a Voith t1205-1 fabric for carrying the web through the apparatus. The web entered the through-air drying apparatus at a consistency of approximately 29%, and left the through-air drying section of the process at a consistency of about 98%.

Leaving the through-air drying apparatus, the web had a caliper of approximately 32 to 36 mils. Caliper of the web was determined by use of an EMVECO 200A Tissue Caliper Tester. Throughout the experimental procedures, caliper was measured at a load of about 2.00 kPa over an area of about 2500 mm$^2$.

Following the through-air drying apparatus, the web was placed between two conveyors and fed around a set of shear-inducing rolls. One conveyor was a style 960 fabric available from the Asten Johnson Corporation. This fabric was travelling at approximately 1600 ft/min. The other conveyor was a style 866B fabric, also available from the Asten Johnson Corporation. Due to the speed differential created by the presence of the shear-inducing rolls, this second fabric was travelling at approximately 1615 ft/min. Both conveyors were at fabric tensions of about 30–35 pounds per linear inch.

The web and the two conveyors traveled together over three shear-inducing rolls, each of which had a 2.25" diameter. the total wrap angle around the three rolls was about 128°. The individual wrap angle for each roll was, 32°, 60°, and 36°, sequentially. The web left the shear-inducing rolls with a caliper of about 20–24 mils.

After the shear-inducing section of the process, the web was calendered in a rubber/steel configuration with a rubber roll covering of about 40 P&J hardness and a nip load of about 15 pli.

The web produced according to the above process was then tested for void volume, geometric mean tensile strength as described in EXAMPLE 1, caliper, and fuzz-on-edge.

Void volume of the resultant sheet was determined according to the following void-volume test. First, the sheet was saturated with a non-polar liquid and the volume of liquid absorbed was measured. The volume of liquid absorbed is equivalent to the void volume within the sheet structure. The void volume is expressed as grams of liquid absorbed per gram of fiber in the sheet.

More specifically, the test includes the following steps. For each single-ply sheet sample to be tested, sheets are selected and a 1 inch×1 inch square (1 inch in the machine direction and 1 inch in the cross machine direction) is cut out. The dry weight of each test specimen is weighed and recorded to the nearest 0.0001 gram.

The specimen is placed in a dish containing POROFILT pore wetting liquid of sufficient depth and quantity to allow the specimen to float freely following absorption of the liquid. (POROFIL™ liquid, having a specific gravity of 1.875 grams per cubic centimeter, available from Coulter Electronics Ltd., Northwell Drive, Luton, Beds., England; Part No. 9902458.) After 10 seconds, the specimen is held at the very edge (1–2 millimeters in) of one corner with tweezers and removed from the liquid. The specimen is held with that corner uppermost and excess liquid is allowed to drip for 30 seconds. The lower corner of the specimen is lightly dabbed (less than ½ second contact) with #4 filter paper (Whatman Ltd., Maidstone, England) in order to remove any excess of the last partial drop. The specimen is immediately weighed, within 10 seconds. The weight is recorded to the nearest 0.0001 gram. The void volume for each specimen, expressed as grams of POROFIL per gram of fiber, is calculated as follows:

Void volume=$[(W_2-W_1)/W_1]$, wherein $W_1$=dry weight of the specimen, in grams, and $W_2$=wet weight of the specimen, in grams. The void volume for all eight individual specimens is determined as described above and the average of the eight specimens is the void volume for the sample.

The fuzz-on-edge test is an image analysis test. The image analysis data are taken from two glass plates made into one fixture. Each plate has a sample folded over the edge with the sample folded in the CD direction and placed over the glass plate. The edge is beveled to 1/16" thickness.

Figure 10:
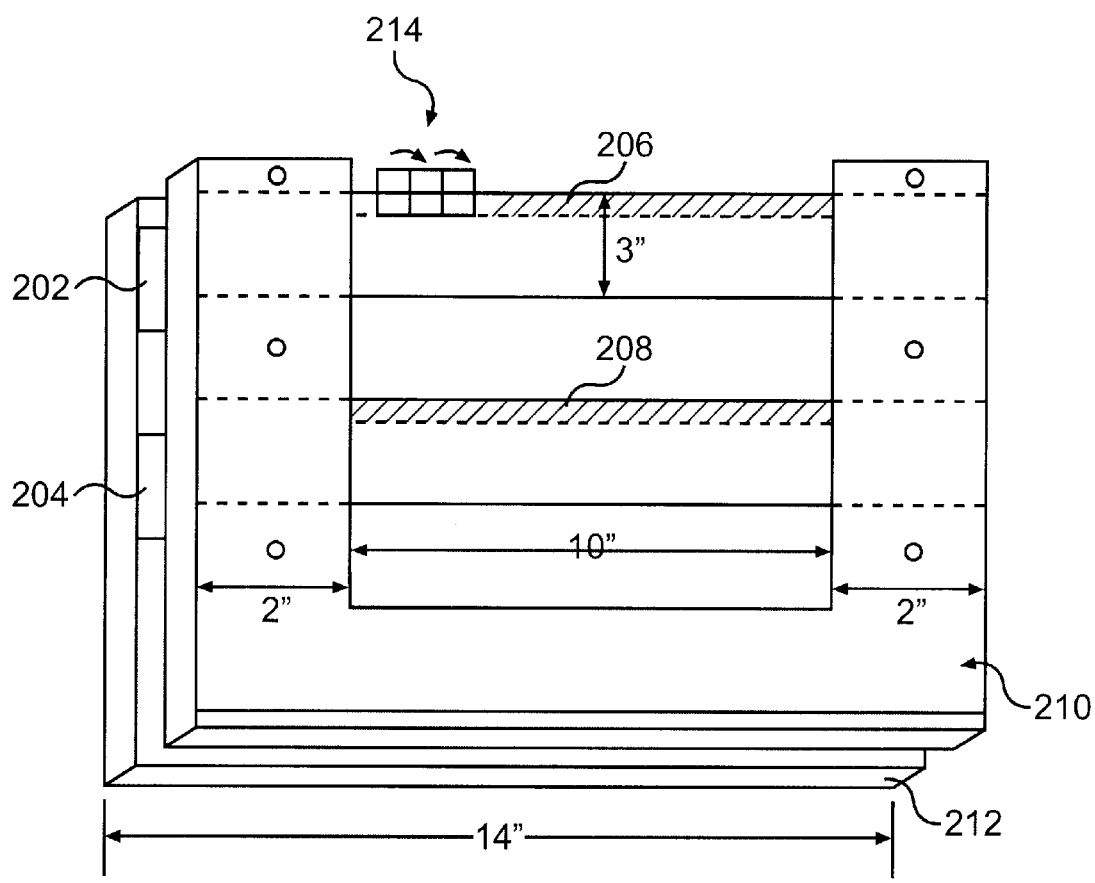
FIG. 10 is a perspective view of the fixture used to conduct the fuzz-on-edge test as described below.

Referring to FIG. 10, one embodiment of a fixture that can be used in conducting the fuzz-on-edge test is shown. As illustrated, the fixture includes a first glass plate 202 and a second glass plate 204. Each of the glass plates have a thickness of ¼ inch. Further, glass plate 202 includes a beveled edge 206 and glass plate 204 includes a beveled edge 208. Each beveled edge has a thickness of 1/16 inch. In this embodiment, the glass plates are maintained in position by a pair of U-shaped brackets 210 and 212. Brackets 210 and 212 can be made from, for instance, ¾ inch finished plywood.

Figure 11:
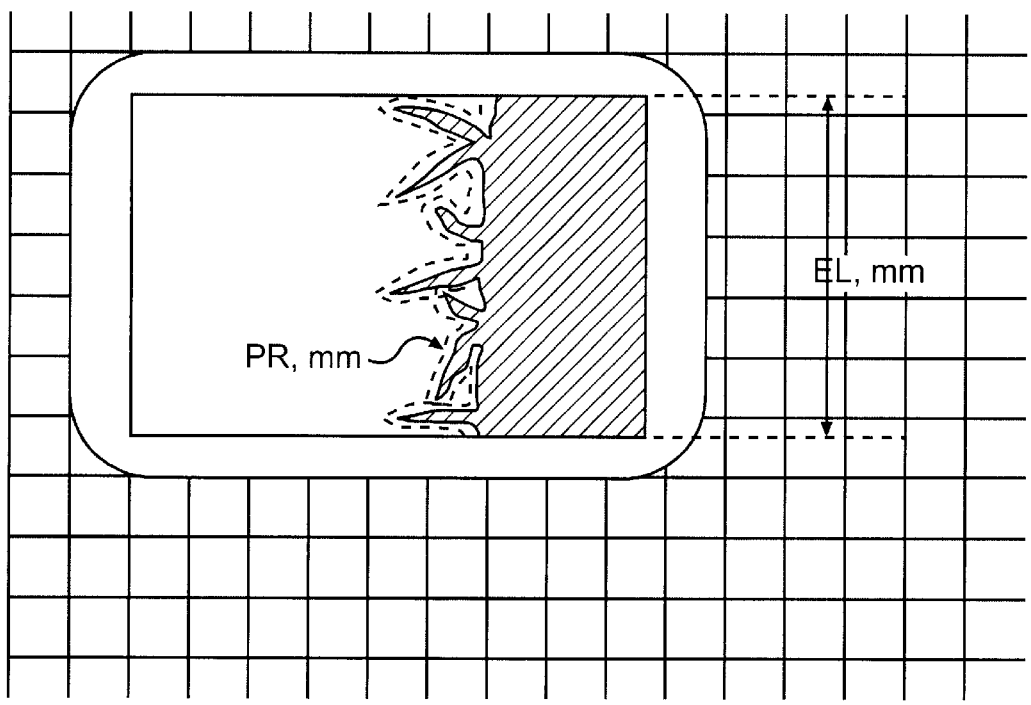
FIG. 11 is a diagrammatical view showing the measurements taken during the fuzz-on-edge test.

During testing, samples are placed over the beveled edges 206 and 208. Multiple images of the folded edges are then taken along the edge as shown at 214. Thirty (30) fields of view are examined on each folded edge to give a total of sixty (60) fields of view. Each view has "PR/EL" measured before and after removal of protruding fibers. "PR/EL" is perimeter per edge-length examined in each field-of-view. FIG. 11 illustrates the measurement taken. As shown, "PR" is the perimeter around the protruding fibers while "EL" is the length of the measured sample. The PR/EL valves are averaged and assembled into a histogram as an output page. This analysis is completed and the data is obtained using the QUANTIMET 970 Image Analysis System obtained from Leica Corp. of Deerfield, Ill. The QUIPS routine for performing this work, FUZZ10, is as follows:

```
Cambridge Instruments QUANTIMET 970 QUIPS/MX:
    VO8.02 USER:
ROUTINE: FUZZIO DATE: May 8, 1981 RUN: 0 SPECI-
    MEN:
NAME=FUZZB
DOES=PR/EL ON TISSUES; GETS HISTOGRAM
AUTH=B. E. KRESSNER
DATE=DEC. 10, 1997
COND=MACROVIEWER; DCI 12X12; FOLLIES PINK
    FILTER; 3×3 MASK 60 MM MICRO-NIKKO,F/4; 20
    MM EXTENSION TUBES; 2 PLATE (GLASS)
    FIXTURE MICRO-NIKKOR AT FULL EXTENSION
    FOR MAX MAG!!!!
    ROTATE CAM 90 deg SO THAT IMAGE ON RIGHT
    SIDE!!
    ALLOWS TYPICAL PHOTO
Enter specimen identity
Scanner (No. 1 Chalnicon LV=0.00 SENS=2.36 PAUSE)
Load Shading Corrector (pattern—FUZZ7)
Calibrate User Specified (Cal Value—9.709 microns per
    pixel)
SUBRTN STANDARD
TOTPREL:=0.
TOTFIELDS:=0.
PHOTO:=0.
MEAN:=0.
If PHOTO=1. then
Pause Message
WANT TYPICAL PHOTO (1=YES; 0=NO)?
Input PHOTO
Endif
If PHOTO=1. then
Pause Message
INPUT MEAN VALUE FOR PR/EL
Input MEAN
Endif
For SAMPLE=1 to 2
If SAMPLE=1. then
STAGEX:=36000.
STAGEY:=144000.
Stage Move (STAGEX,STAGEY)
Pause Message
please position fixture
Pause
STAGEX:=120000.
STAGEY:=144000.
Stage Move (STAGEX,STAGEY)
Pause Message
please focus
Detect 2D (Darker than 54, Delin PAUSE)
STAGEX:=36000.
STAGEY:=144000.
Endif
If SAMPLE=2. then
STAGEX:=120000.
STAGEY:=44000.
Stage Move ( STAGEX,STAGEY)
Pause Message
please focus
Detect 2D (Darker than 54, Delin)
STAGEX:=36000.
STAGEY:=44000.
Endif
Stage Move (STAGEX,STAGEY)
Stage Scan (X Y
    scan origin STAGEX STAGEY
    field size 6410.0 78000.0
    no of fields 30 1)
For FIELD
If TOTFIELDS=30. then
Scanner (No. 1 Chalnicon AUTO-SENSITIVITY LV=0.01)
Endif
Live Frame is Standard Image Frame
Image Frame is Rectangle (X: 26, Y: 37, W: 823, H: 627,)
Scanner (No. 1 Chalnicon AUTO-SENSITIVITY LV=0.01)
Image Frame is Rectangle (X: 48, Y: 37, W: 803, H: 627,)
Detect 2D (Darker than 54, Delin)
Amend (OPEN by 10 )
Measure field—Parameters into array FIELD
BEFORPERI:=FIELD PERIMETER
Amend (OPEN by 10)
Measure field—Parameters into array FIELD
AFTPERIM:=FIELD PERIMETER
PROVEREL:=((BEFORPERI—AFTPERIM)/
    (I.FRAME.H*CAL.CONST))
TOTPREL:=TOTPREL+PROVEREL
TOTFIELDS:=TOTFIELDS+1.
If PHOTO=1. then
If PROVEREL>(0.95000 * MEAN) then
If PROVEREL<(1.0500 * MEAN) then
Scanner (No. 1 Chainicon AUTO-SENSITIVITY LV=0.01
    PAUSE)
Detect 2D ( Darker than 53 and Lighter than 10, Delin
    PAUSE)
Endif
Endif
Endif
Distribute COUNT vs PROVEREL (Units MM/MM)
into GRAPH from 0.00 to 5.00 into 20 bins, differential
Stage Step
Next FIELD
Next
Print " "
Print "AVE PR-OVER-EL (UM/UM)=", TOTPREL/
    TOTFIELDS
Print " "
Print "TOTAL NUMBER OF FIELDS=", TOTFIELDS
Print " "
Print "FIELD HEIGHT (MM)=", I.FRAME.H *
    CAL.CONST/1000
Print " "
Print " "
Print Distribution (GRAPH, differential, bar chart, scale=
    0.00)
For LOOPCOUNT=1 to 26
Print " "
Next
END OF PROGRAM
```

The product sheet exhibited the following characteristics:
basis weight—31.4 gsm (bone dry)
geometric mean tensile strength—531 grams/3" width (177 g/in) measured with a 2 inch gap between grips
caliper—0.0159 inches
void volume—12.0 g fluid/g fiber
Fuzz-on-Edge (FOE)—2.165 perimeter ratio/edge length

EXAMPLE 3

An uncreped through-air-dried web was made as described in Example 2, with the exception that the three shear-inducing rolls of Example 2 were replaced with three 4.5" diameter rolls and the total wrap angle around the three rolls was about 90°. Additionally, the web was calendered in a rubber/steel configuration with a rubber roll covering of about 40 P&J hardness and a nip load of about 25 pli.

The product sheet exhibited the following characteristics:
basis weight—32.07 gsm (bone dry)
geometric mean tensile strength—621 grams/3" width (207 g/in) measured with a 2 inch gap between grips
caliper—0.0180 inches
Fuzz-on-Edge (FOE)—2.357 perimeter ratio/edge length

EXAMPLE 4

An uncreped through-air-dried web was made as described in Example 2, with the exception that the three shear-inducing rolls of Example 2 were replaced with three 4.5" diameter rolls and the total wrap angle around the three rolls was about 163°. Additionally, the web was calendered in a rubber/steel configuration with a rubber roll covering of about 40 P&J hardness and a nip load of about 25 pli.

The product sheet exhibited the following characteristics:
basis weight—31.80 gsm (bone dry)
geometric mean tensile strength—583 grams/3" width (194 g/in) measured with a 2 inch gap between grips
caliper—0.0156 inches
Fuzz-on-edge (FOE)—2.548 perimeter ratio/edge length

EXAMPLE 5

An uncreped through-air-dried web was made as described in Example 2, with the exception that the three shear-inducing rolls of example 2 were replaced with three 4.5" diameter rolls and the total wrap angle around the three rolls was about 163°. Additionally, the web was calendered in a rubber/steel configuration with a rubber roll covering of about 40 P&J hardness and a nip load of about 0 pli.

The product sheet exhibited the following characteristics:
basis weight—32.14 gsm (bone dry)
geometric mean tensile strength—616 grams/3" width (205 g/in) measured with a 2 inch gap between grips
caliper—0.0189 inches
Fuzz-on-edge (FOE)—2.726 perimeter ratio/edge length

EXAMPLE 6

An uncreped through-air-dried web was made as described in Example 2, with the exception that the three shear-inducing rolls of example 2 were replaced with one 4.5" diameter roll and the total wrap angle around the roll was about 60°. Additionally, the web was calendered in a rubber/steel configuration with a rubber roll covering of about 40 P&J hardness and a nip load of about 100 pli.

The product sheet exhibited the following characteristics:
basis weight—32.39 gsm (bone dry)
geometric mean tensile strength—635 grams/3" width (212 g/in) measured with a 2 inch gap between grips
caliper—0.0163 inches p1 Fuzz-on-edge (FOE)—2.332 perimeter ratio/edge length These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A paper product comprising:
a nonwoven base web, said base web comprising a paper web containing pulp fibers, said base web having a fuzz-on-edge of greater than about 2.2 mm/mm.

2. A paper product as defined in claim 1, wherein said base web has a basis weight of greater than 20 gsm.

3. A paper product as defined in claim 2, wherein said base web has a void volume greater than 12 g/g.

4. A paper product as defined in claim 1, wherein said base web has a fuzz-on-edge of greater than about 2.5 mm/mm.

5. A paper product as defined in claim 1, wherein said paper product comprises a single-ply product.

6. A paper product as defined in claim 1, wherein said base web has a geometric mean tensile strength of greater than about 170 g/in.

7. A paper product as defined in claim 1, wherein said base web has a geometric mean tensile strength of greater than about 200 g/in.

8. A paper product as defined in claim 1, wherein said base web comprises an uncreped, through-air-dried web.

9. A paper product as defined in claim 1, wherein the paper web comprises a stratified web.

10. A paper product as defined in claim 9, wherein the paper web includes a middle layer positioned between a first outer layer and a second outer layer, the first and second outer layers comprising softwood fibers.

11. A paper product as defined in claim 1, wherein the base web has been subjected to a shearing force in an amount sufficient for the web to have the fuzz-on-edge property of greater than about 2.2 mm/mm.

12. A paper product as defined in claim 11, wherein the base web has been subjected to the shearing force by being placed in between a first moving conveyor and a second moving conveyor, and guiding the first moving conveyor and the second moving conveyor around a shear-inducing roll while the base web is positioned between the conveyors.

13. A paper product as defined in claim 12, wherein the first and second conveyors are wrapped around the shear-inducing roll at least 50°.

14. A paper product comprising:
a paper web containing pulp fibers, the paper web being an uncreped, through-air-dried web, the paper web having a fuzz-on-edge of greater than about 2.2 mm/mm.

15. A paper product as defined in claim 14, wherein the paper web has a basis weight of greater than about 20 gsm.

16. A paper product as defined in claim 15, wherein the paper web has a void volume of greater than 12 g/g.

17. A paper product as defined in claim 14, wherein the paper web has a fuzz-on-edge of greater than about 2.5 mm/mm.

18. A paper product as defined in claim 14, wherein the paper product comprises a single-ply product.

19. A paper product as defined in claim 14, wherein the paper web has a geometric mean tensile of greater than about 170 g/in.

20. A paper product as defined in claim 14, wherein the paper web has a geometric mean tensile of greater than about 200 g/in.

21. A paper product as defined in claim 14, wherein the paper web comprises a stratified web, the stratified web including a middle layer positioned between a first outer layer and a second outer layer, the first outer layer and the second outer layer containing softwood fibers.

22. A paper product as defined in claim 14, wherein the paper web has been subjected to a shearing force in an amount sufficient for the web to have a fuzz-on-edge of greater than about 2.2 mm/mm.

23. A paper product as defined in claim 22, wherein the paper web has been subjected to the shearing force by being placed in between a first moving conveyor and a second moving conveyor and guiding the first moving conveyor and the second moving conveyor around a shear-inducing roll while the paper web is positioned between the conveyors.

24. A paper product as defined in claim 14, wherein the paper web further comprises synthetic fibers.

25. A paper product as defined in claim 14, wherein the paper web further comprises thermomechanical pulp.

26. A paper product comprising:
a paper web containing softwood fibers, the paper web having been subjected to a shearing force in an amount sufficient for the paper web to have a fuzz-on-edge of greater than about 2.2 mm/mm.

27. A paper product as defined in claim 26, wherein the paper web has a void volume of greater than 12 g/g and has a basis weight of greater than about 20 gsm.

28. A paper product as defined in claim 26, wherein the paper web has a fuzz-on-edge of greater than about 2.5 mm/mm.

29. A paper product as defined in claim 26, wherein the paper web has a geometric mean tensile strength of greater than about 170 g/in.

30. A paper product as defined in claim 26, wherein the paper web comprises an uncreped, through-air-dried web.

31. A paper product as defined in claim 26, wherein the paper web has been subjected to the shearing force by being placed in between a first moving conveyor and a second moving conveyor and guiding the first moving conveyor and the second moving conveyor around a shear-inducing roll while the paper web is positioned between the conveyors.

* * * * *